(12) United States Patent
Sherwood et al.

(10) Patent No.: US 7,412,347 B2
(45) Date of Patent: Aug. 12, 2008

(54) METHOD AND APPARATUS FOR MEASURING PHYSICAL PARAMETERS

(75) Inventors: Robert A. Sherwood, El Paso, TX (US); Roy A. Griffin, El Paso, TX (US)

(73) Assignee: Sherwood Engineering Design Services, Inc., El Paso, TX (US)

( * ) Notice: Subject to any disclaimer, the term of this patent is extended or adjusted under 35 U.S.C. 154(b) by 0 days.

(21) Appl. No.: 11/654,354

(22) Filed: Jan. 17, 2007

(65) Prior Publication Data
US 2007/0180902 A1      Aug. 9, 2007

Related U.S. Application Data

(60) Provisional application No. 60/766,485, filed on Jan. 23, 2006.

(51) Int. Cl.
*G01K 1/00* (2006.01)
(52) U.S. Cl. ........................ 702/130; 702/127
(58) Field of Classification Search .................. 702/127
See application file for complete search history.

(56) References Cited

U.S. PATENT DOCUMENTS

| | | | |
|---|---|---|---|
| 4,441,107 A | 4/1984 | Chaborski et al. | |
| 4,841,458 A * | 6/1989 | Levine et al. | ................ 702/133 |
| 4,916,643 A | 4/1990 | Ziegler et al. | |
| 5,171,091 A | 12/1992 | Krüger et al. | |
| 5,420,397 A | 5/1995 | Weiss et al. | |
| 5,422,462 A | 6/1995 | Weiss et al. | |
| 5,708,256 A | 1/1998 | Montagnino et al. | |
| 5,770,836 A | 6/1998 | Weiss | |
| 5,902,044 A | 5/1999 | Pricer et al. | |
| 5,929,344 A | 7/1999 | Hays et al. | |
| 6,223,132 B1 | 4/2001 | Kornhaas et al. | |
| 2002/0008101 A1 * | 1/2002 | Hauschulz | ................... 219/494 |

* cited by examiner

*Primary Examiner*—John E Barlow, Jr.
*Assistant Examiner*—Jonathan Moffat
(74) *Attorney, Agent, or Firm*—Hamilton, Brook, Smith & Reynolds, P.C.

(57) ABSTRACT

An apparatus and corresponding method measure physical parameters using a plurality of low-cost sensors coupled in series is provided. These sensors can be thermal sensors for measuring the temperature of a heating pad. Different types of sensors to measure temperature, moisture, pressure, or state change of a switch may be employed. Such sensors may be distributed throughout a building to concurrently monitor multiple physical parameters at numerous locations. The sensors are easily manufactured, thus reducing sensor cost. Costs are further reduced by the use of two wires to connect the series of sensors. Moreover, the wires can be run easily through conduit or cable troughs.

37 Claims, 14 Drawing Sheets

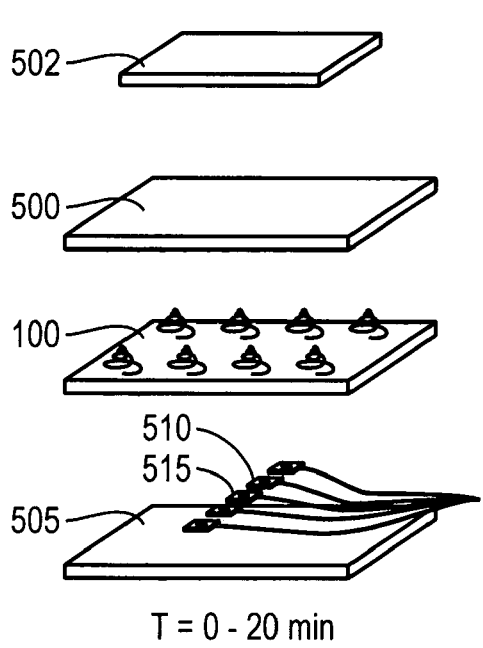
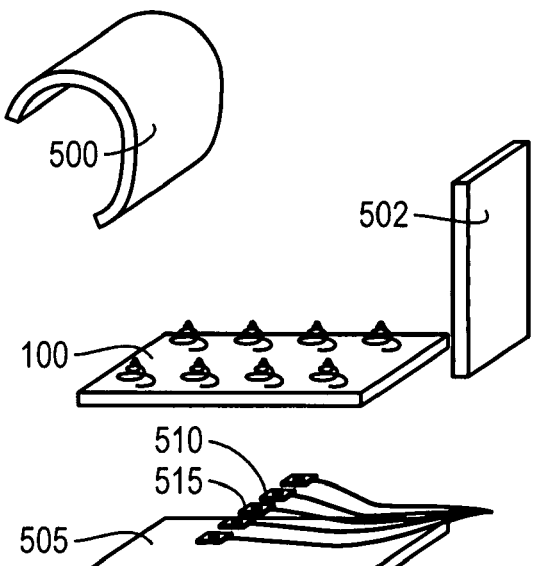
T = 0 - 20 min
T > 20 min
FIG. 5A-1
FIG. 5A-2
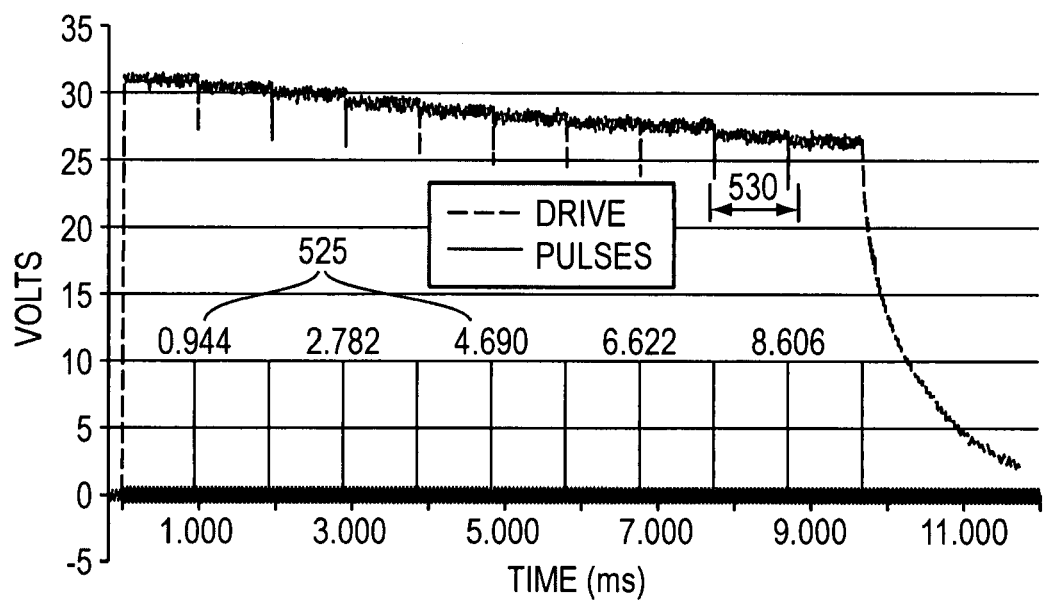
FIG. 5B

| FIGURE 3. CALCULATED SENSOR TEMPERATURES | | |
|---|---|---|
| TIME (ms) | DELTA T | SENSOR TEMPERATURE |
| (msec) | (msec) | (DEG. F) |
| 0.944 | 0.944 | 154 |
| 1.788 | 0.844 | 160 |
| 2.782 | 0.994 | 152 |
| 3.684 | 0.902 | 156 |
| 4.69 | 1.006 | 151 |
| 5.674 | 0.984 | 152 |
| 6.622 | 0.948 | 154 |
| 7.584 | 0.962 | 153 |
| 8.606 | 1.022 | 150 |
| 9.616 | 1.010 | 151 |

CADMIUM SULFIDE LIGHT SENSOR

POTENTIOMETER POSITION SENSOR

CAPACITIVE TYPE RELATIVE HUMIDITY SENSOR

SWITCH STATE SENSOR

METHOD AND APPARATUS FOR MEASURING PHYSICAL PARAMETERS

RELATED APPLICATION

This application claims the benefit of U.S. Provisional Application No. 60/766,485, filed on Jan. 23, 2006. The entire teachings of the above application are incorporated herein by reference.

BACKGROUND OF THE INVENTION

Heating pads are normally used to apply heat to parts of the body to aid in healing or for comfort. Most consist of a remote control device and a heating device. The remote control is typically plugged into a household AC power outlet and regulates the temperature of the heating device. The remote control has a user interface, typically pushbuttons or a multi-position switch, so the user can turn the heating device power on or off and select a desired temperature. The heating device consists of a heating means, usually a flexible insulated wire, a means of preventing unsafe temperatures, and a cover to prevent user contact with the electrical components.

One method of controlling temperature is to use a thermostat that opens the heating power circuit when a fixed temperature is reached. However, such thermostats can be relatively expensive, costing approximately twenty-two cents each. In addition to heat from the heating wire, an additional source of heat is applied to the thermostat by means of a resistive heating source with a power set by the remote control. A low heat is achieved by passing all of the current that is flowing through the heating wire through the additional heating source, causing the thermostat to open at a lower temperature than it would if it were heated by the heating wire alone. To achieve the highest desired temperature, no power is applied to the resistive source, and for a mid range temperature power is applied to the resistive heating source for one-half cycle of the AC line.

Typically a second or third thermostat is used in separate sections of the heating pad to prevent unsafe temperatures from occurring due to uneven heating. Such an unsafe condition can occur when a portion of the pad is covered, preventing heat from radiating. The additional thermostats open the heating wire circuit before an unsafe temperature occurs. In these cases, the temperature is monitored in only limited locations and the measured temperature is not representative of the average temperature of the heating pad. Further, thermostats generate electrical noise when they open and close and are expensive.

Another method of controlling temperature is to use a separate sensing wire that is concentrically wound around the heating wire. The resistance of the sensing wire varies with temperature by a known amount. Therefore, by sensing the wire resistance, the temperature can be calculated. The control device constantly monitors the sensing wire resistance and calculates the wire temperature. If the temperature is above the user-selected value, power is removed from the heating wire. If the temperature is below the user-selected value, power is applied to the heating wire.

Because the sensing wire is distributed over the entire heating wire, its resistance is a measure of the average temperature of the wire. To prevent localized hot spots from reaching a dangerous temperature, the insulation between the heating and sensing wires is made of a material that melts or becomes electrically conductive when unsafe temperatures are approached. A circuit in the remote control monitors the resistance between the heating and sensing wires and removes power from the heating wire if the resistance falls below a value corresponding to an unsafe temperature.

The sensing wire resistance changes are small, typically 0.25% per degree Fahrenheit. The variation in the room temperature resistance of the sensing wire is large enough that an initial calibration must be done on each heating pad, thereby adding manufacturing expense. Further, the pad must be discarded and replaced if localized heating occurs that melts the insulation between the heating and sensing wires. Moreover, the sensing wire does not accurately sense the pad temperature because it is in close proximity to the heating wire, and is separated from the surface of the pad by the outer insulation layer and the pad cover components.

SUMMARY OF THE INVENTION

An apparatus and corresponding method measure physical parameters using a plurality of low-cost sensors coupled in series. The sensors each have a circuit with a time constant relating to a physical parameter to be measured by the sensors. Each circuit causes measurement signals to be generated in series. Further, a module provides a drive signal to the sensors to generate the respective measurement signals. The module also measures the physical parameters based on a metric associated with the respective measurement signals.

The time constant of the circuit may be defined by the characteristics of a transducer or a combination of the transducer and at least one passive circuit element. Further, the time constant may be changed, thereby affecting the metric associated with the respective measurement signal generated by the sensor. Or, the time constant may be selectively changed so that one sensor can measure multiple physical parameters.

The sensors include a transducer that may be a temperature transducer to measure temperature, a moisture transducer to measure moisture or humidity, a pressure transducer to measure pressure, or a switch to measure the state change of a switch. The physical parameters may be measured by using a pulse, period between pulses, amplitude, voltage, voltage change, or current.

To reduce wiring costs, the series of sensors are electrically coupled with the module via two wires which provide the drive signal. Measurement signals are transmitted between the sensors and module. Three or more wires may also be used.

In order to convert the metric to an operational parameter relating to the respective physical parameter, the module must include memory to store conversion data. The module further includes an interface to provide the operational parameter to a system configured to influence the physical parameters to be measured. Such a physical parameter is the temperature of a heating pad.

The module includes circuitry coupled to the sensors to generate pulses based on the measurement signals and measures the physical parameters as a function of a time period between adjacent pulses. Moreover, the module includes an interface to interact with a system that influences the physical parameters to be measured.

The module provides the drive signal to the sensors by providing the drive signal to a first sensor in the series of sensors, which, in turn, provides a drive signal to a next sensor in the series of sensors, and so forth, except for the last sensor in the series. The sensors generate the measurement signals by affecting the drive signal in a manner that is measurable by the module.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 5A-1 is a diagram illustrating a heating pad and controller constructed according to the circuit described in FIG. 2B with felt insulation applied to the top and bottom of the heating pad, respectively.

FIG. 5A-2 is a diagram illustrating a heating pad and controller constructed according to the circuit described in FIG. 2B with felt insulation applied to the bottom of the heating pad and the felt insulation on top of the heating pad removed.

FIG. 5B is a signal diagram illustrating a drive signal and the pulses present on the PULSES input to the controller at an average heating pad surface temperature of 137 degrees Fahrenheit.

DETAILED DESCRIPTION OF THE INVENTION

A description of example embodiments of the invention follows. Although the present description is given in terms of a heating pad application, it should be understood that the present invention has applications in other areas requiring remote sensing of physical parameters.

Figure 1A:
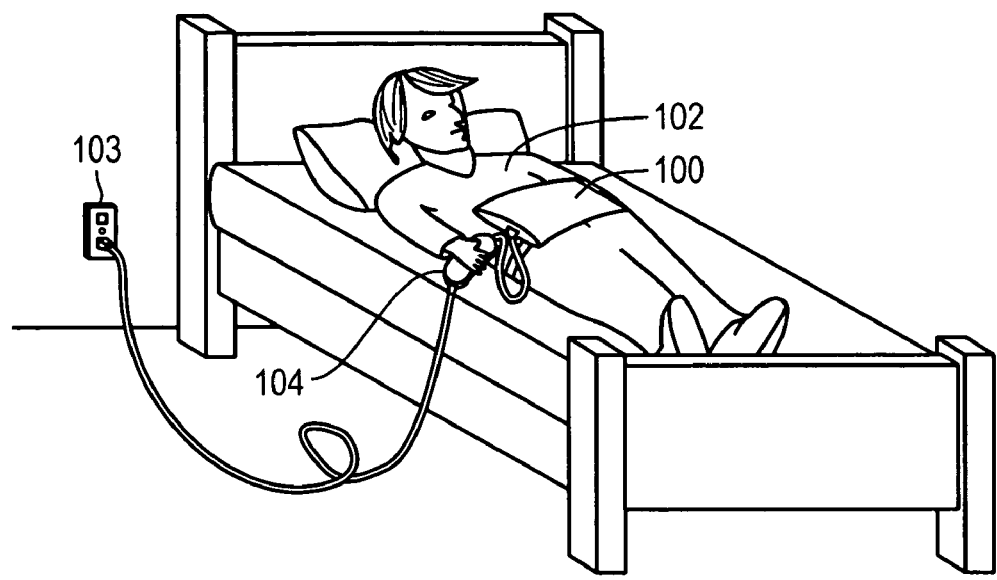
FIG. 1A is an illustration of a user applying a heating pad plugged into a household AC electrical outlet by placing the heating pad on a part of the user that can benefit from heat therapy.

FIG. 1A is an illustration of a user 102 applying a heating pad 100 plugged into a household AC electrical outlet 103 by placing the heating pad 100 on a part of the user 102 that can benefit from heat therapy. The user 102 may control the heating pad 100 through a remote control 104, more generally referred to herein as a module. A module may contain more or fewer components than in a remote control, depending on the functionality required.

Figure 1B:
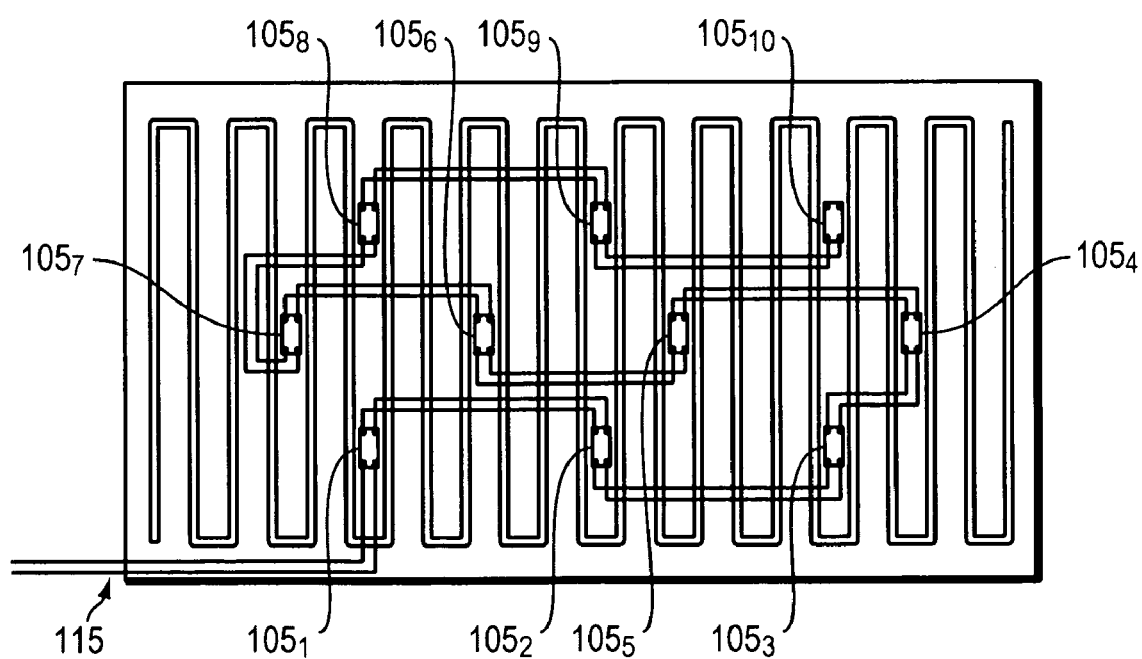
FIG. 1B is an illustration of a heating pad showing the location of a series of ten remote sensors in the heating pad.

FIG. 1B is an illustration of a heating pad 100 showing the location of a series of ten remote sensors $105_1$-$105_{10}$ in the heating pad 100. The number of sensors 105 in the series of remote sensors $105_1$-$105_n$ in a heating pad 100 can vary by design and application. The heating wire 110 is distributed over the heating pad 100 and connected to the remote control (not shown). A pair of wires 115 carries signals to and from the series of remote sensors $105_1$-$105_{10}$ and is also connected to the remote control (not shown).

Figure 2A:
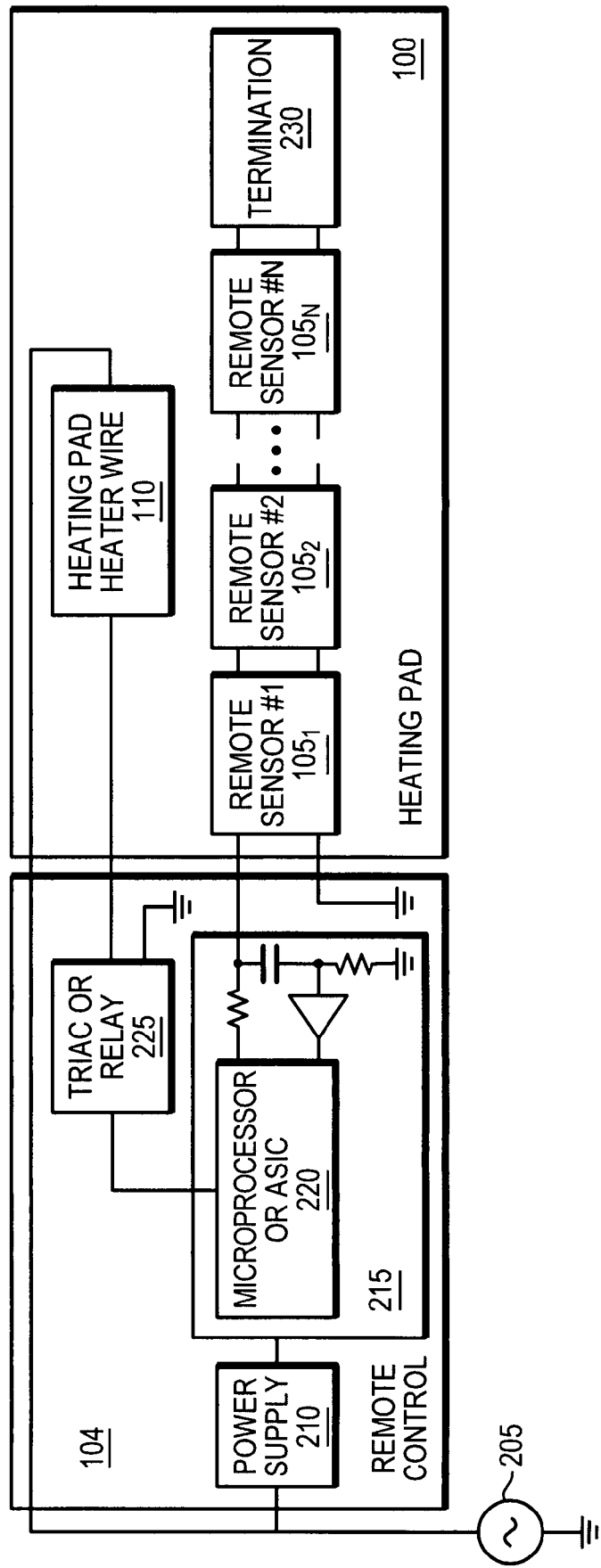
FIG. 2A is a block diagram illustrating the heating pad and a remote control.

FIG. 2A is a block diagram of the heating pad 100 and a remote control 104. A source of power 205, typically AC power from a household outlet (103 in FIG. 1A), is connected to the remote control 104 and provides power to the heating wire 110 and, through a power supply 210, to the remote control circuitry 215. A microprocessor or application specific integrated circuit (ASIC) 220 controls power to the heating pad 100 by turning a triac 225 on and off and sends a interrogation signal to and receives signals representing each sensor's 105 temperature from the heating pad temperature sensors $105_1$-$105_n$. A termination 230 provides a load to the last sensor $105_n$ similar to the load provided to the other sensors $105_1$-$105_{n-1}$.

Figure 2B:
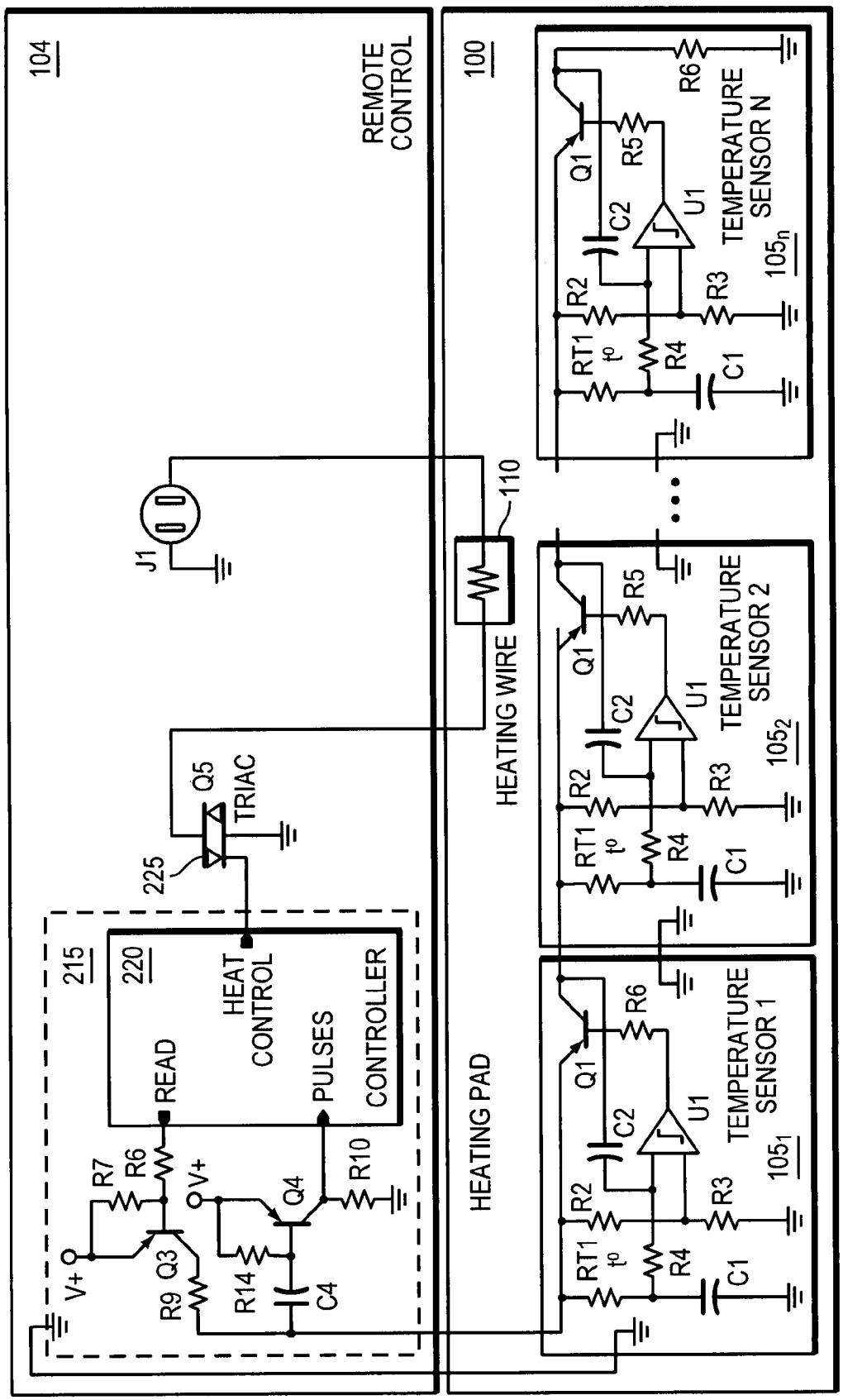
FIG. 2B is a circuit diagram illustrating the remote control in series with a plurality of temperature sensor elements.

FIG. 2B is a circuit diagram illustrating the remote control in series with a plurality of temperature sensor elements. A source of AC power (not shown) (205 in FIG. 2A) is connected to the remote control 104 through J1. A power supply (not shown) provides DC power to the remote control circuitry 215. Means of selecting temperature and turning the heating pad on and off are also not shown. Periodically, the controller 220 in the remote control 104 applies a voltage to the first sensor $105_1$ in the heating pad 100 through resistor R9 by pulling the READ line to ground, turning on PNP transistor Q3 whose emitter is connected to a source of DC voltage. This applies a reference voltage to the positive input of comparator U1 by means of a resistive voltage divider comprised of R2 and R3. The voltage from the controller is also applied to thermistor RT1 and begins charging capacitor C1 connected to the negative input of comparator U1. When the voltage on the negative input exceeds the voltage on the positive input, the output of U1 will be pulled to ground turning on PNP transistor Q1. Q1 collector supplies voltage to the next sensor $105_2$ and through capacitor C2, a positive pulse to the negative input of U1 to insure a rapid turn on of U1 and Q1. Because C1 resists a rapid change in voltage, R4 is needed to allow the positive feedback effect of the pulse through C2 to induce rapid turn on of the voltage to the next sensor.

Capacitor C1 charges at a rate given by:

$$V_{C1} = V_{in}(1 - e^{T/R_{th}C})$$

Where:
$V_{in}$ is the voltage applied from the remote control
$V_{C1}$ is the voltage across C1
$R_{th}$ is the resistance of thermistor RT1
C is the capacitance of C1
T is time since voltage was applied
Solving for time T:

$$T = R_{th} C \ln(1 - V_{C1}/V_{in})$$

Comparator U1 begins switching on when Vc1 exceeds the positive input voltage $V_{th}$.

$$V_{th}/V_{in}=R3/(R2+R3)$$

Because $V_{th}$ is substantially equal to $V_{C1}$:

$$T=R_{th}C\ln(1-V_{th}/V_{in}) \text{ and}$$

$$T=R_{th}C\ln(1-R3/(R2+R3))$$

Except for a slight error caused by comparator U1 offset voltage, the delay from application of voltage Vin to the application of voltage to the subsequent sensor 105 is proportional to $R_{th}$ and independent of the sensor's input voltage. The voltage applied to subsequent sensors 105 decreases as the voltage drop across R9 increases due to increased current as more sensors 105 are switched on but the error in switching time is small.

As each sensor 105 is switched, a rapid increase in current through R9 occurs. Resistor R6 on the output of the last sensor $105_n$ provides a termination R6 (230 of FIG. 2A) so the current increase when the last sensor $105_n$ is switched on is substantially equal to the other sensors $105_1$-$105_{n-1}$. Capacitor C4, resistor R14, transistor Q4 and resistor R10 respond the rapid change in current to produce a pulse at the PULSES input to the controller 220.

Figure 3:
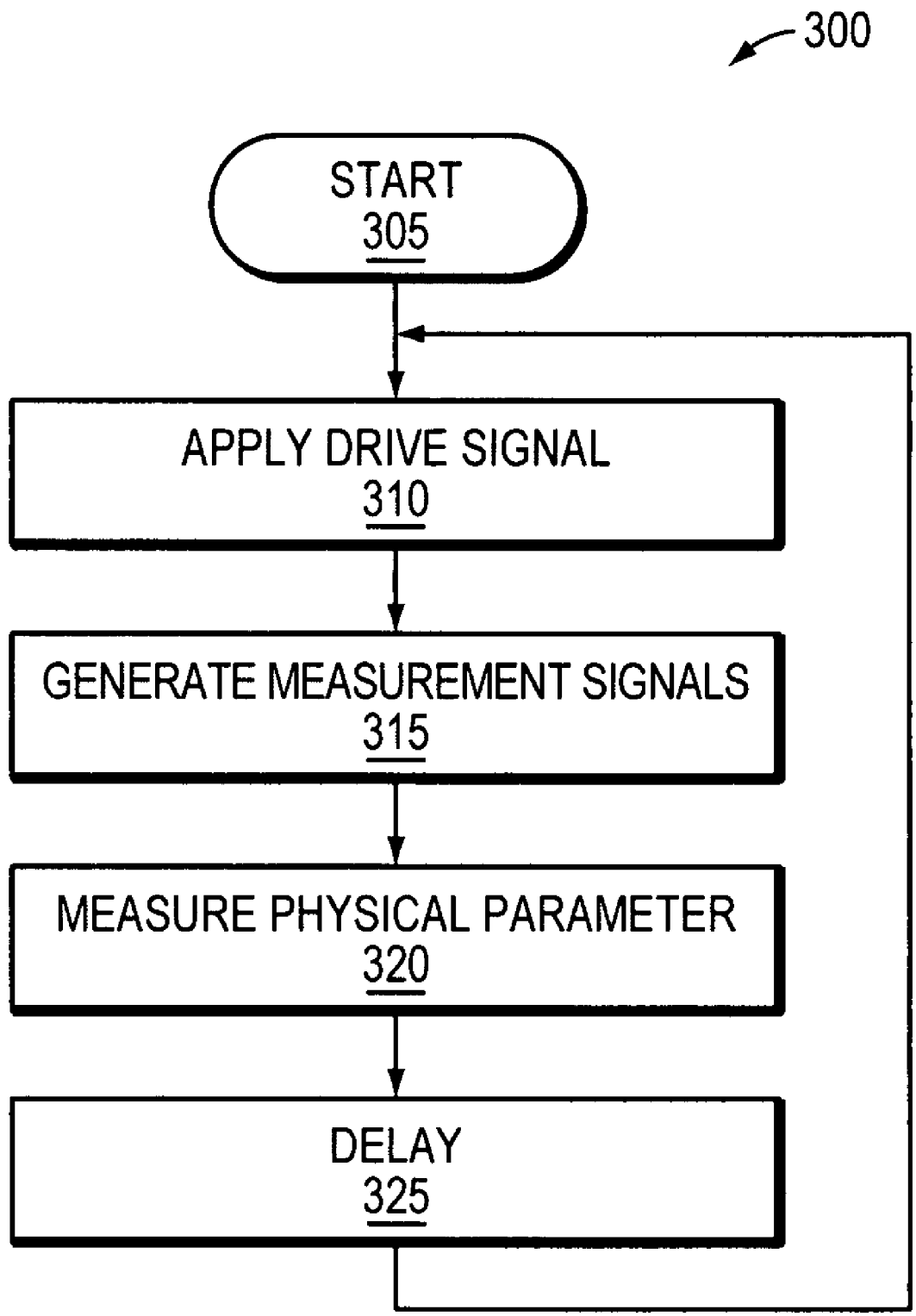
FIG. 3 is a flow diagram illustrating a method for measuring physical parameters.

FIG. 3 is a flow diagram 300 illustrating a method for measuring physical parameters. After starting 305, a drive signal is applied 310 to a series of remote sensors $105_1$-$105_n$. Each sensor 105 in the series of remote sensors $105_1$-$105_n$ generates a measurement signal 315 relating to a physical parameter. The measurement signal is then processed 320 to determine the value of the physical parameter. After a delay 325, the process repeats, starting with the application of the drive signal 310.

Figure 4:
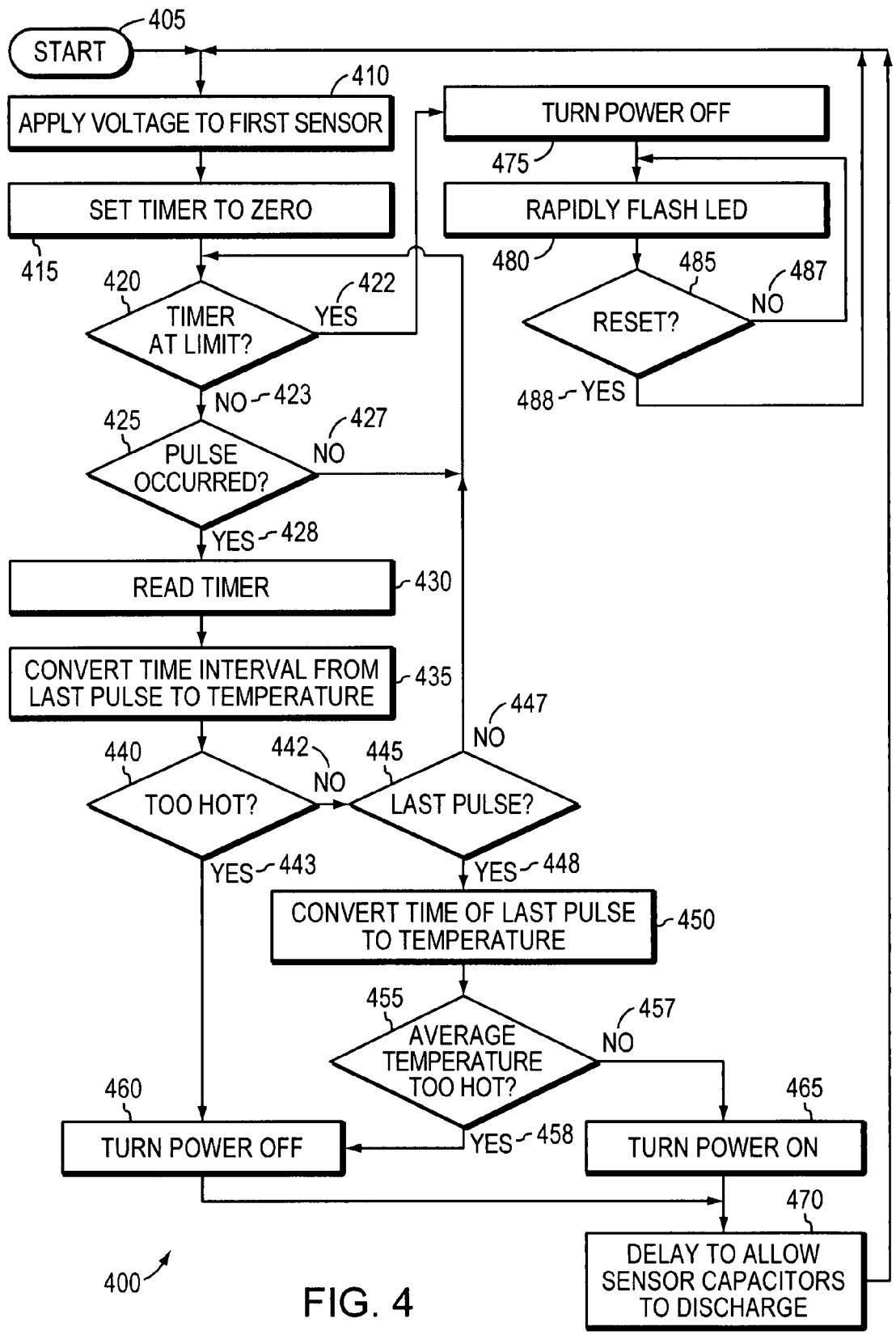
FIG. 4 is a flow diagram illustrating a method for controlling the temperature of a heat pad.

FIG. 4 is a detailed flow diagram 400 illustrating a method for controlling the temperature of a heating pad 100. The process starts 405 when the user 102 turns on the heating pad 100 and selects a desired temperature. The controller 220 then applies a voltage 410 to the first sensor $105_1$ in the series of sensors $105_1$-$105_n$ and sets a timer to zero 415. The value of the timer is then checked 420 to insure a pulse has been received within a maximum time limit. Because the timer has just been set to zero 415, the answer is no 423.

The controller 220 then checks 425 for the presence of a pulse and, if one has not occurred 427, returns to check if the timer is at the maximum limit 420. If there are no faults in the series of sensors $105_1$-$105_n$, a pulse eventually will be found 428. The value of the time will be read 430. The time difference between the last pulse will be converted to a temperature value 435. The controller 220 then determines if the temperature is too hot 440. If the temperature is too hot 443, power is turned off 460 so that the heating pad 100 may cool. If the temperature is not too hot 442 (below a safe limit), the controller 220 checks 445 if this pulse was from the last sensor $105_n$. If not 447, the controller 220 returns to check the timer limit 420 and wait 425 for the next pulse. If the last pulse was received 448, the controller 220 converts 450 the time of the last pulse to determine the average sensor temperature.

The controller 220 then determines if the average temperature is too hot 455. If the average temperature is above 458 the user selected temperature (too hot), power to the heating pad 100 is turned off 460. If it is below 457 the user selected value, power to the heating pad 100 is turned on 465. In either case, the controller 220 delays 470 for a time sufficient to discharge the capacitors in the series of sensors $105_1$-$105_n$ and returns to apply 410 voltage to the first sensor $105_1$ for the next measurement.

If all of the pulses are not received in an interval that is less than the maximum time all pulses should occur in a properly operating system, the "Timer at Limit?" 420 is answered yes 422, power is removed 475 from the heating pad 100, and a light emitting diode (LED) or other indicating device flashes 480 rapidly to indicate a catastrophic failure. No further operation is possible until power is removed causing the controller 220 to reset 485.

If the controller 220 is reset 488, the controller 220 returns to apply 410 voltage to the first sensor $105_1$ for the next measurement. If the controller 220 is not reset 487, the LED or other indicating device, continues to flash 480 indefinitely or until the main AC power source 103 is disconnected from the controller 220.

FIG. 5A-1 is a diagram illustrating a heating pad 100 and controller 220 (not shown) constructed according to the circuit described in FIG. 2B with felt insulation 500, 505 applied to the top and bottom of the heating pad 100, respectively. The heating pad 100 was tested by insulating it between two layers of one inch thick felt 500, 505. Temperatures of the heating pad 100 were measured with an array of 5 thermocouples 510 mounted on one inch square copper plates 515 centered across the short axis of the heating pad 100 at the center of the long axis between the bottom felt insulation 505 and the heating pad 100. An aluminum plate 502 was placed on the top felt insulation 500 to ensure the bottom piece of felt insulation 505, thermocouples 510, heating pad 100 and top felt insulation 500 were held together. Measurements were taken for twenty minutes while the heating pad 100 was insulated between the layers of felt 500, 505.

FIG. 5A-2 is a diagram illustrating a heating pad 100 and controller 220 (not shown) constructed according to the circuit described in FIG. 2B with felt insulation 505 applied to the bottom of the heating pad 100, and the top felt insulation 500 and aluminum plate 502 removed. After twenty minutes, the top felt insulation 500 and aluminum plate 502 were removed, exposing the top of the heating pad 100 to ambient air, as illustrated in FIG. 5A-2. The heating pad 100 then continued to operate until the end of testing when power was turned off.

FIG. 5B is a signal diagram illustrating a drive signal 520 and the pulses 525 present on the PULSES input to the controller 220 at an average heating pad surface temperature of 137 degrees Fahrenheit. Each pulse $525_1$-$525_{10}$ is generated by its respective sensor 105 in the series of sensors $105_1$-$105_{10}$ illustrated in FIG. 1B. The controller 220 measures the time difference 530 between adjacent pulses 525 and calculates the temperature of each sensor 105. The time to the last pulse $525_{10}$ is a measure of the average temperature of each sensor $105_1$-$105_n$ and is compared to the desired temperature selected by the user 102.

If the average temperature is below the desired temperature, Triac Q5 is turned on to apply power to the heating wire 110. If the temperature is above the desired value, triac Q5 turns off power to the heating wire 110. Because the controller "knows" the temperature of each sensor $105_1$-$105_n$, power is also turned off if the temperature of any sensor 105 exceeds a safe value. If a break in the sensor wiring 115 occurs, or a sensor 105 fails to respond in a reasonable time, temperature cannot be measured accurately and power is also removed from the heating wire 110 to prevent an unsafe overheating condition.

After receiving the last pulse 525, the controller 220 delays for a time to allow capacitors C1 and C2 to discharge. Then the process repeats.

Figures 5C, 5D:
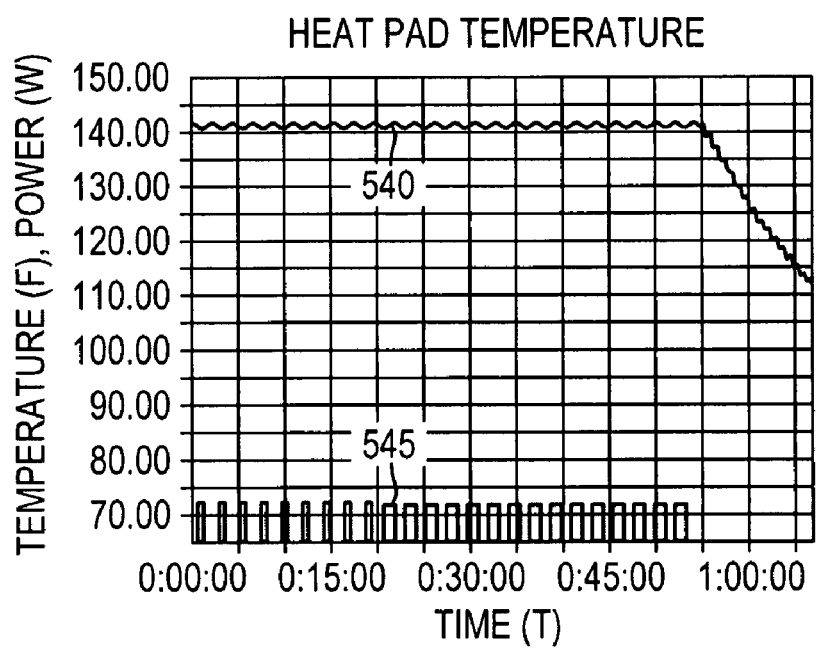
FIG. 5C is a table illustrating the time of each pulse, the time difference from the previous pulse, and the calculated temperature of each sensor in the heating pad.
FIG. 5D is a signal diagram illustrating power on duty cycle and average temperature versus time for the testing conditions of the heating pad as illustrated in FIGS. 5A-1 and 5A-2.

FIG. 5C is a table illustrating the time of each pulse 525, the time difference 530 from the previous pulse 525, and the calculated temperature of each sensor in the heating pad.

FIG. 5D is a signal diagram illustrating power on duty cycle and average temperature versus time for the testing conditions of the heating pad as illustrated in FIGS. 5A-1 and 5A-2. First, as in FIG. 5A-1, the temperature of the heating pad 100 was allowed to stabilize. Then, from zero to twenty minutes, readings of the five thermocouple 510 temperatures were averaged and plotted as a function of time. Temperature is shown in the upper curve 540 and the state of heating wire current in the lower curve 545.

At twenty minutes, the top layer of felt was removed, as in FIG. 5A-2. Note the increase in the "on" time of the heating wire current needed, during each measurement cycle, to maintain the temperature of the heating pad 100 as more heat is radiated into the ambient air. This test demonstrates that an average heating temperature was maintained with only a small error when the amount of heat lost from the heating pad 100 changed. The average temperature of the surface of the heating pad 100, as measured by the array of thermocouples 510 and plotted in FIG. 5D, is lower than the average temperature of the sensors, as provided in FIG. 5D, due to the thermal drop across the material surrounding the heating wire.

FIGS. 6A-6H are circuit diagrams illustrating alternate sensor configurations that may be employed to measure different physical parameters.

Figure 6A:
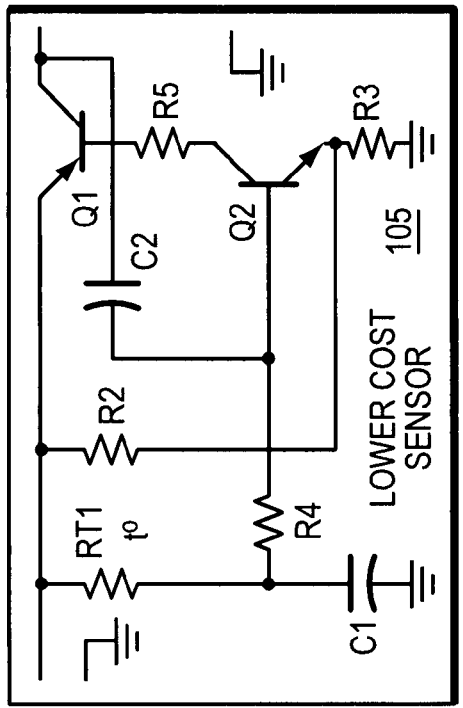
FIGS. 6A-6H are circuit diagrams illustrating alternate sensor configurations that may be employed to measure different physical parameters.

FIG. 6A is a circuit diagram illustrating a sensor that responds to temperature in the manner previously described.

Figure 6B:
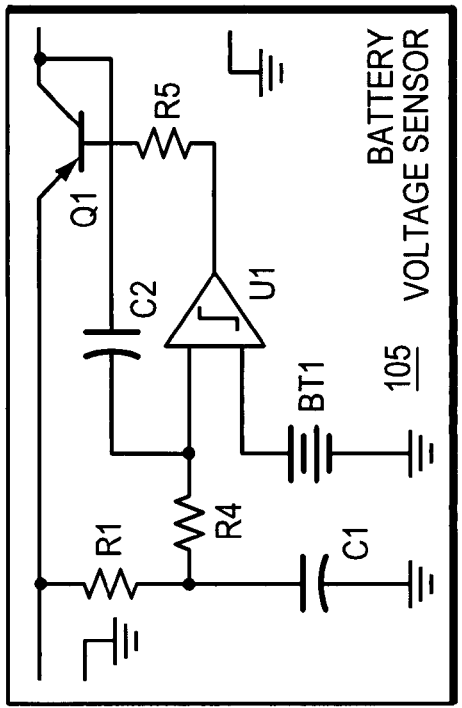

FIG. 6B is a circuit diagram illustrating a lower-cost circuit in which the comparator U1 has been replaced by NPN transistor Q2. Operation is similar to the comparator except that the base to emitter voltage of the transistor must be overcome before transistor Q2 turns on. If the supply voltage is large compared to the base emitter drop, the error is acceptable.

Other embodiments of the invention can be used to measure physical parameters in applications other than heating pads.

Figure 6C:
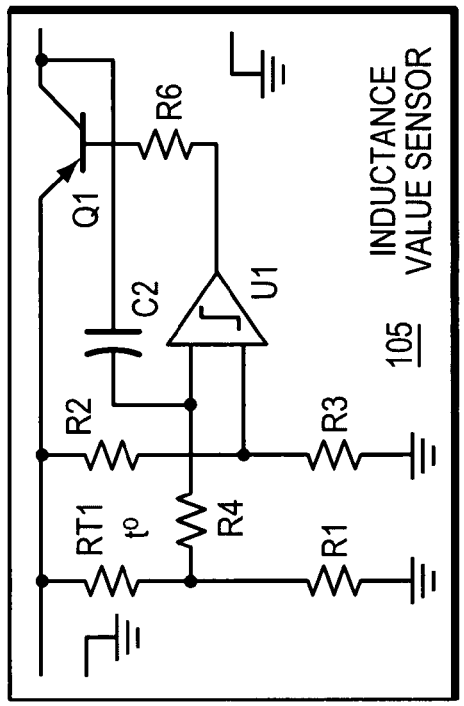

FIG. 6C is a circuit diagram illustrating an inductor L1 in place of the thermistor RT1 and a resistor R1 in place of the capacitor C1 of FIG. 6B. When voltage is applied to the sensor 105, current through the inductor L1 will increase with time at a rate depending on the inductance value. As inductor current increases, the voltage drop across resistor R1 increases until comparator U1 turns on. A core inside the coil L1 could be attached to a movable object so the position of the movable object varies the position of the core and therefore the value of the inductance. The delay between application of sensor voltage and the pulse created when comparator U1 turns on would then be a measure of the position of the movable object.

Figure 6D:
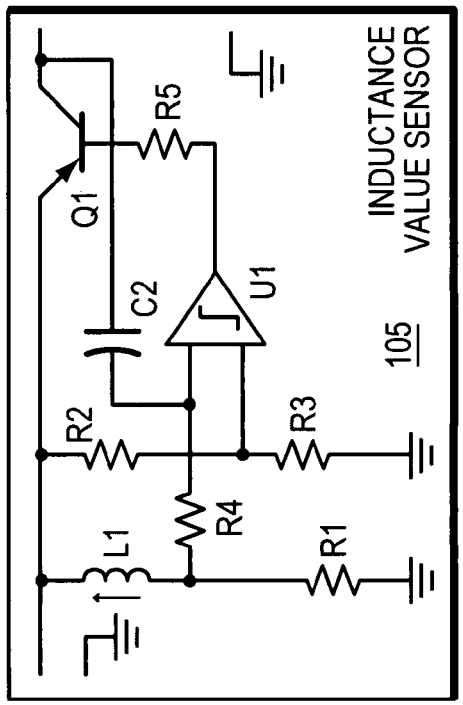

FIG. 6D is a circuit diagram illustrating a method of using the invention to determine the value of a DC voltage. Time to switch on the comparator U1 is determined by the time taken to charge capacitor C1, through R1 to the value of the DC voltage. An AC voltage could also be measured by first rectifying and filtering it to generate a DC voltage.

Figure 6F:
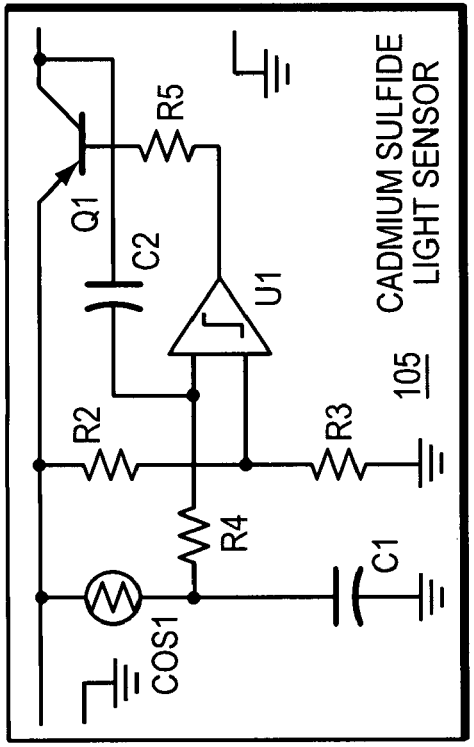
Figure 6H:
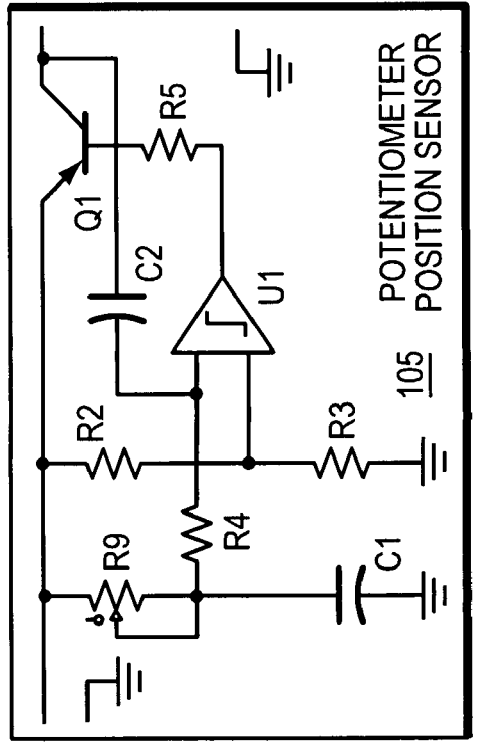
Figure 6E:
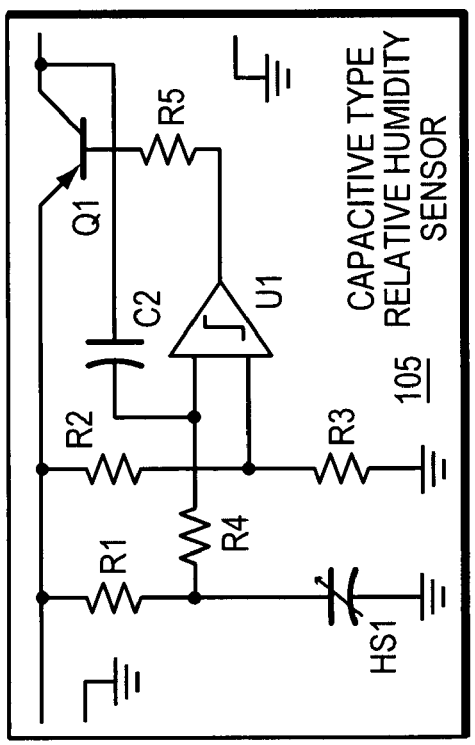

FIG. 6E is a circuit diagram illustrating a sensor that can be used to measure relative humidity. The capacitance is related to relative humidity in a known way so that the time to charge the capacitor HS1 and switch on comparator U1 can be use to measure humidity. Another type of humidity sensor varies resistance in response to relative humidity and could be used in the circuit of FIG. 6A by replacing RT1 with a resistive humidity sensor.

FIG. 6F is a circuit diagram illustrating a cadmium sulphide light sensor CDS1 in place of the thermistor RT1 in the circuit of FIG. 4A. Because the value of light sensor resistance is related to the light level in a known way, the time delay of the pulse produced can be used to measure light level.

Figure 6G:
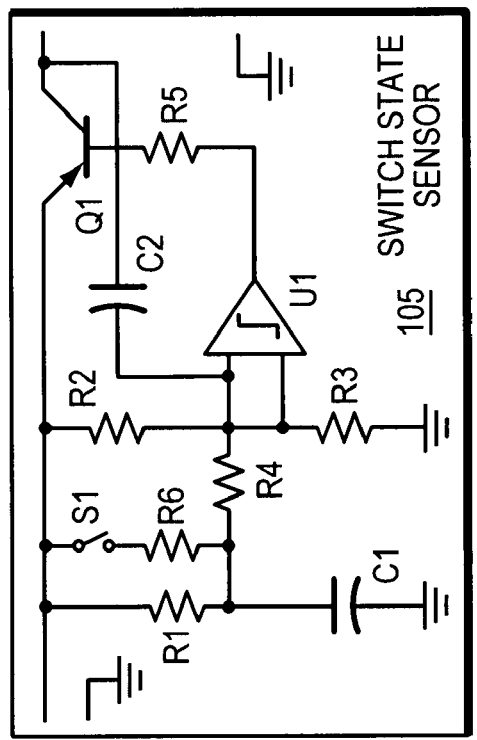

FIG. 6G is a circuit diagram illustrating a circuit used to determine the state of a switch S1. In one application, the switch S1 could be attached to a door so an alarm is sounded when the door is opened. When the switch S1 is open capacitor C1 is charged through R1 producing a pulse of a known delay. When the switch S1 is closed, resistor R6 is connected in parallel with R1 and a shorter delay is produced.

FIG. 6H is a circuit diagram illustrating replacing resistor R1 with a rheostat R9. The value of the rheostat R9 can be varied by a physical connection to a movable object. For example, a rheostat with a rotating shaft could be attached to a float to determine the level of a liquid.

Figure 7A:
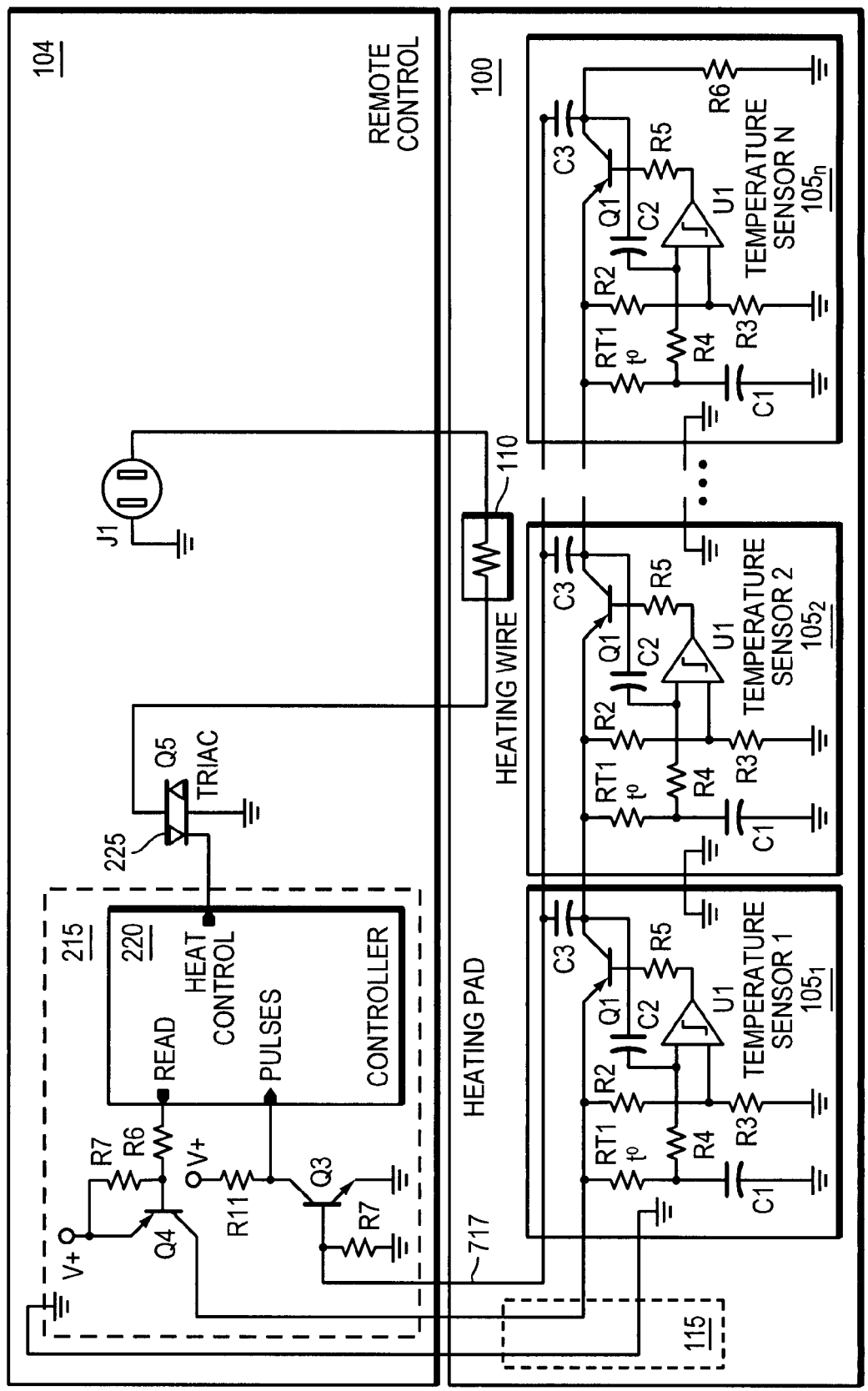
FIGS. 7A-7B are circuit diagrams illustrating a third wire, in addition to the pair of wires, added to the series of sensors, to return pulses to the controller and to provide the reference voltage to comparator, respectively.

FIG. 7A is a circuit diagram illustrating a third wire 717, in addition to the pair of wires 115, added to the series of sensors $105_1$-$105_n$, to return pulses to the controller 220. The resistor R9 of FIG. 2B in series with the sensor drive is eliminated so the voltage applied to subsequent sensors 105 is increased, allowing more sensors 105 to be connected in the series of sensors $105_1$-$105_n$ before the sensor input voltage drops to an unacceptable level. Without the series resistor R9, the main source of voltage drop is the saturation voltage of PNP transistor Q2.

Figure 7B:
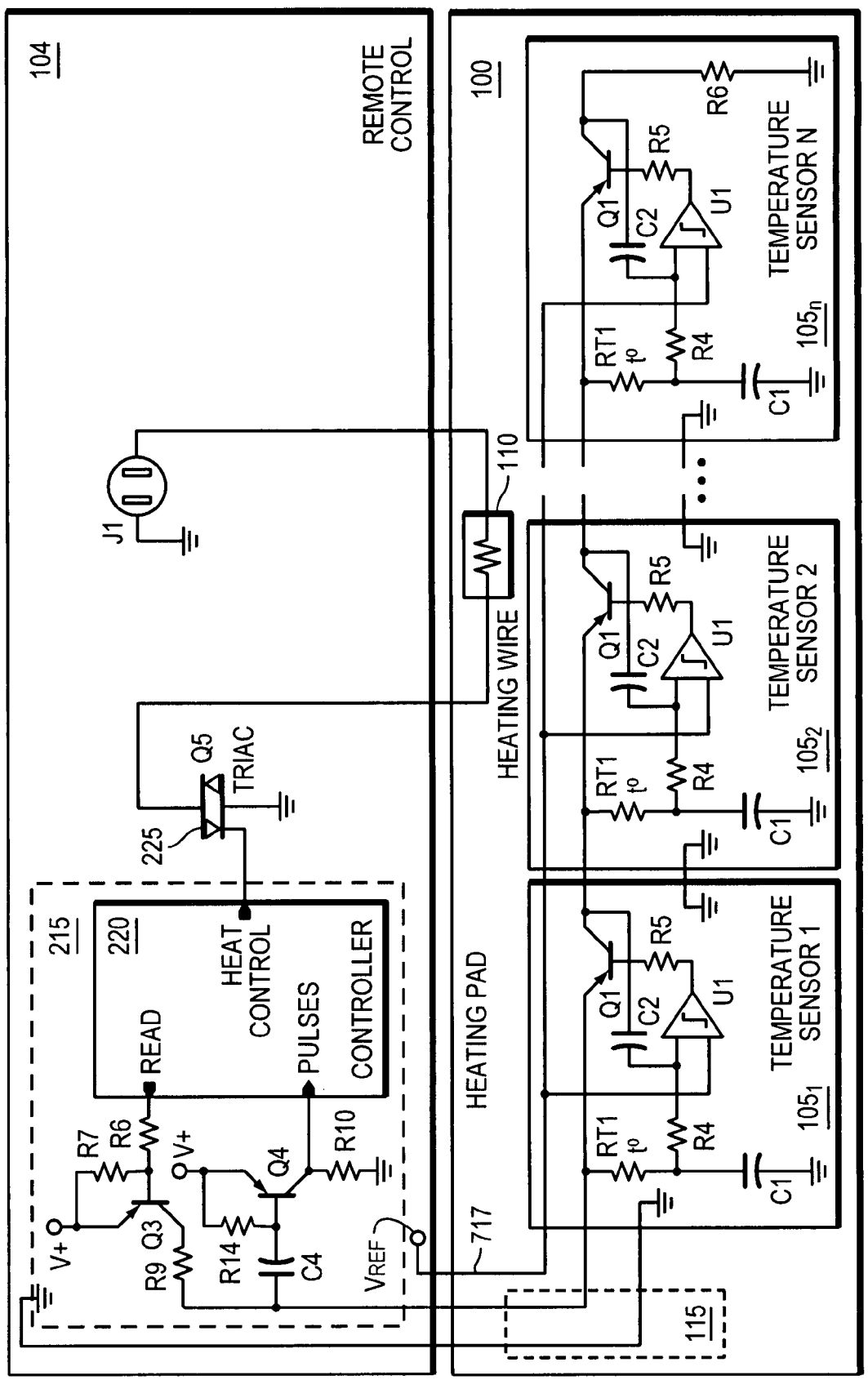

FIG. 7B is a circuit diagram illustrating a third wire 717, in addition to the pair of wires 115, added to the series of sensors $105_1$-$105_n$ to provide the reference voltage to comparator U1. A single precision reference voltage could be generated in the remote control 104. Because the sensor does not compensate for changes in input voltage, increased complexity would be required in the controller 220 to adjust the calculated temperature as a function of the location of the sensor 105 in the series of sensors $105_1$-$105_n$. Sensors 105 further from the controller 220 would have a lower input voltage due to an increased drop across resistor R9 and a longer pulse interval.

Figure 8A:
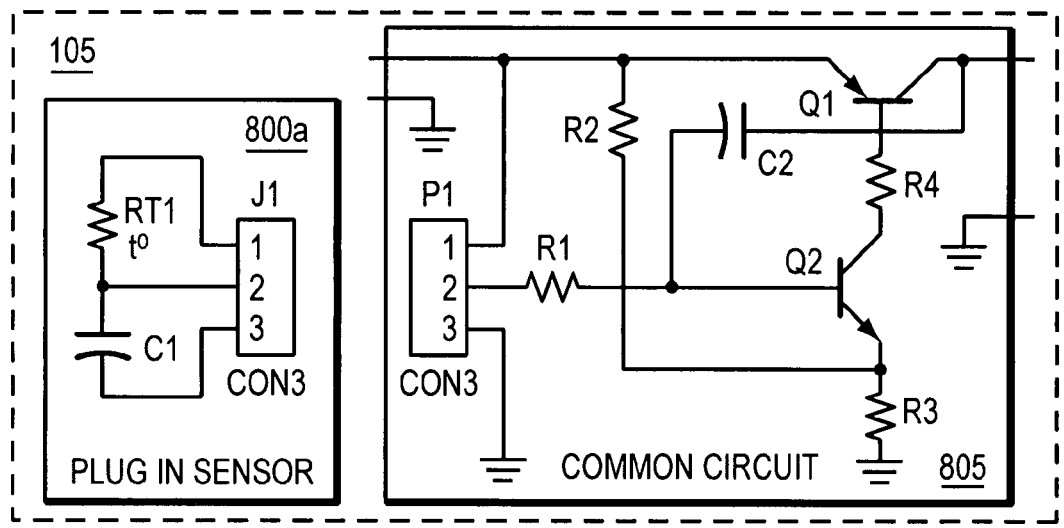
FIG. 8A is a circuit diagram illustrating an optional plug-in sensing element consisting of a thermistor and capacitor.

FIG. 8A is a circuit diagram illustrating an optional plug-in sensing element 800a consisting of a thermistor RT1 and capacitor C1. Using this approach, different types of sensing elements 800 could be plugged into a common sensor circuit 805 so a series of sensors $105_1$-$105_n$ could be installed and the parameter sensed at each sensor 105 changed by simply changing the plug-in sensing element 800.

Figure 8B:
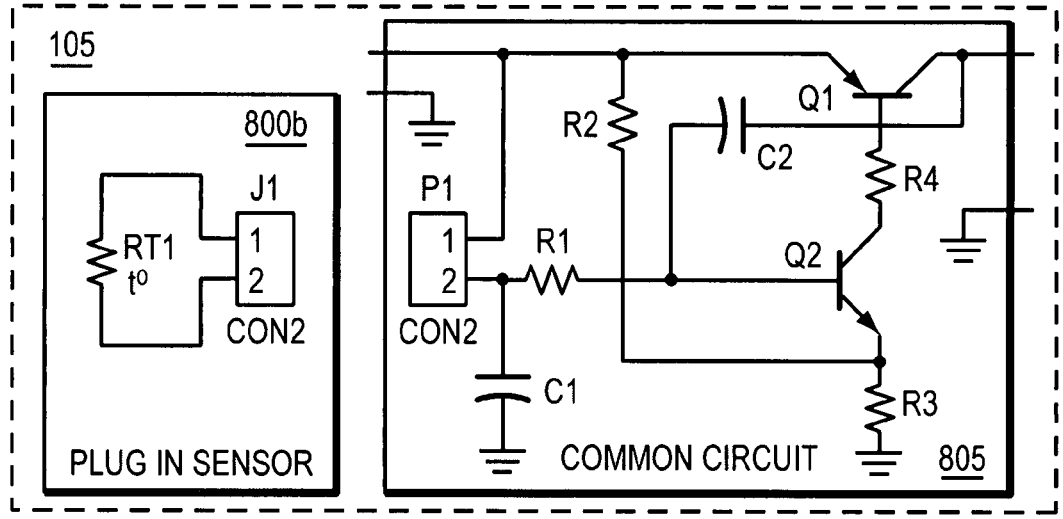
FIGS. 8B-8C are circuit diagrams illustrating configurations similar to that in FIG. 8A but with a thermistor or capacitor only in the plug-in sensing element, respectively
Figure 8C:
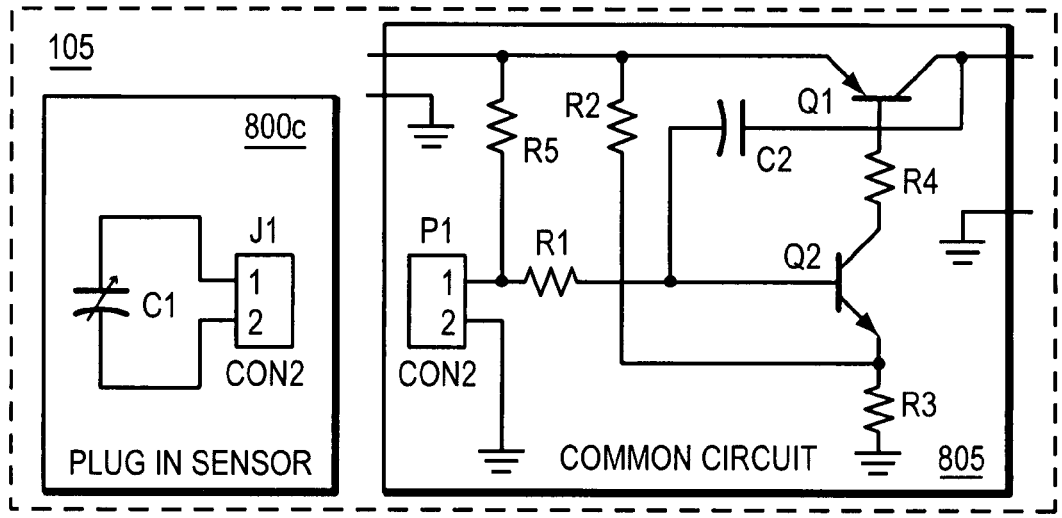

FIGS. 8B and 8C are circuit diagrams illustrating configurations similar to that in FIG. 8A but with a thermistor RT1 or capacitor C1 only in the plug-in sensing element 800b, 800c, respectively.

Figure 9:
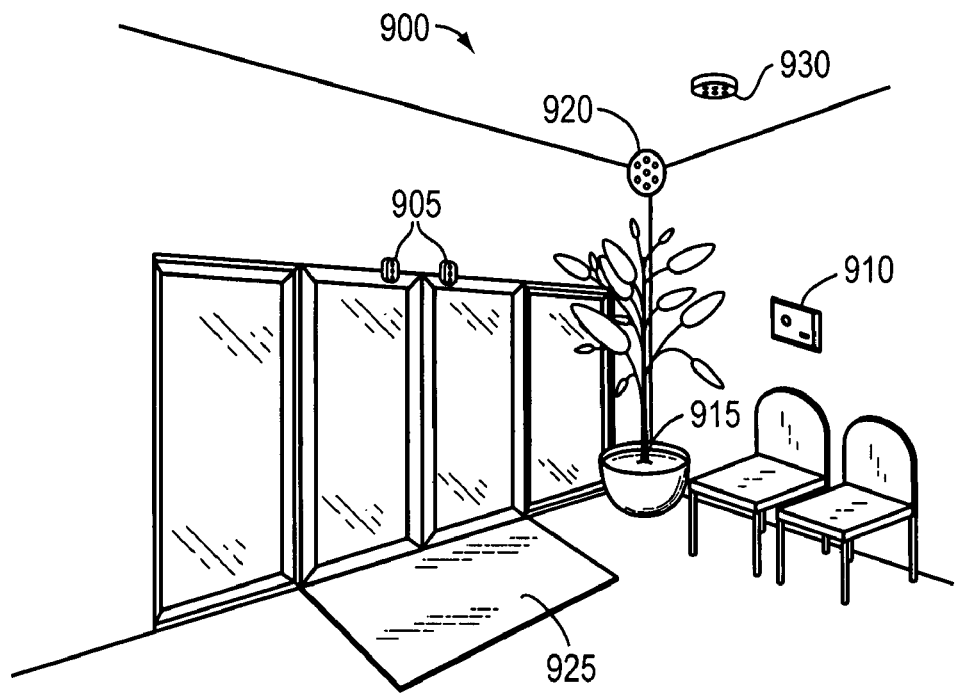
FIG. 9 is an illustration of a lobby of a building with a series of sensors deployed.

FIG. 9 is an illustration of a lobby 900 of a building with a series of sensors $105_1$-$105_n$ deployed. Different types of sensors, such as those illustrated by FIGS. 6A to 6H, may be used in combination in a series of sensors. The sensors measure the status of the entrance doors 905, room temperature 910, humidity 915, light 920, a switch 925, and battery voltage 930. However, the controller or module must know what type of sensor is located at each position in the series of sensors so that the difference between pulses may be converted to the metric appropriate for that sensor. The difference between pulses (or other metric associated with the respective measurement signals) based on the type of sensor being employed. Further, the module (not shown) that processes the measurement signals knows the expected timing (or other meaning) to sense an alarm or other condition associated with any one of or multiple sensors.

Figure 10:
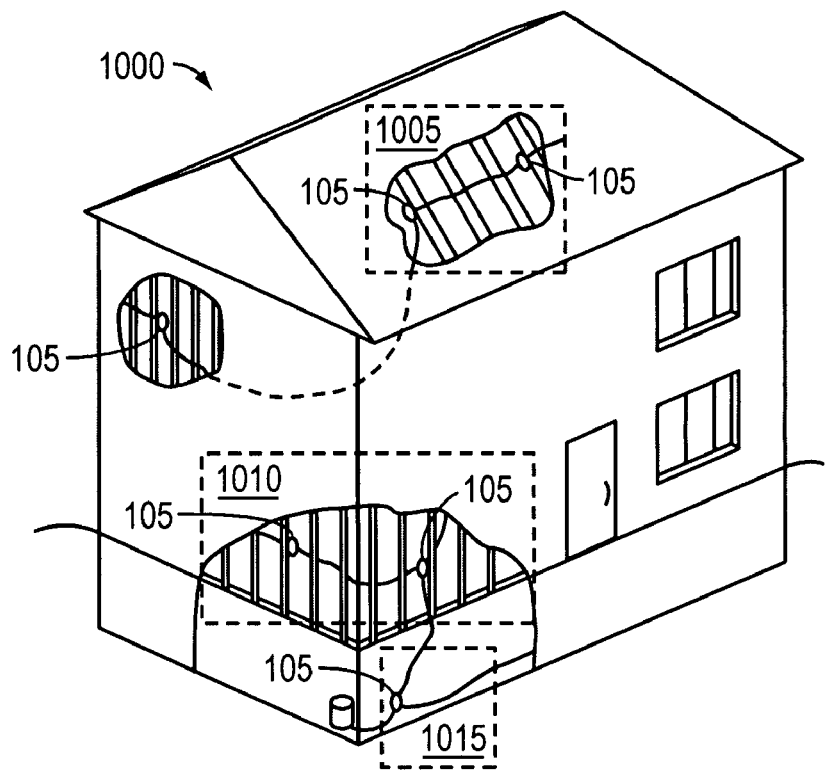
FIG. 10 is an illustration of a structure, such as a home, with sensors deployed.

FIG. 10 is an illustration of a structure, such as a home 1000, with sensors deployed. One application 1005 can be to use sensors 105 to measure temperature at selected locations, such as an attic, to detect a fire. Another application 1010 can to use sensors 105 to measure the temperature in each room so the airflow from the heating or air conditioning could be directed where it is needed. Further applications can be to place additional sensors 105 in a basement 1015 or inside walls 1010 or in an attic 1005 to measure humidity and to provide an early indication of a potential for mold growth to protect the value of a home.

Figure 11:
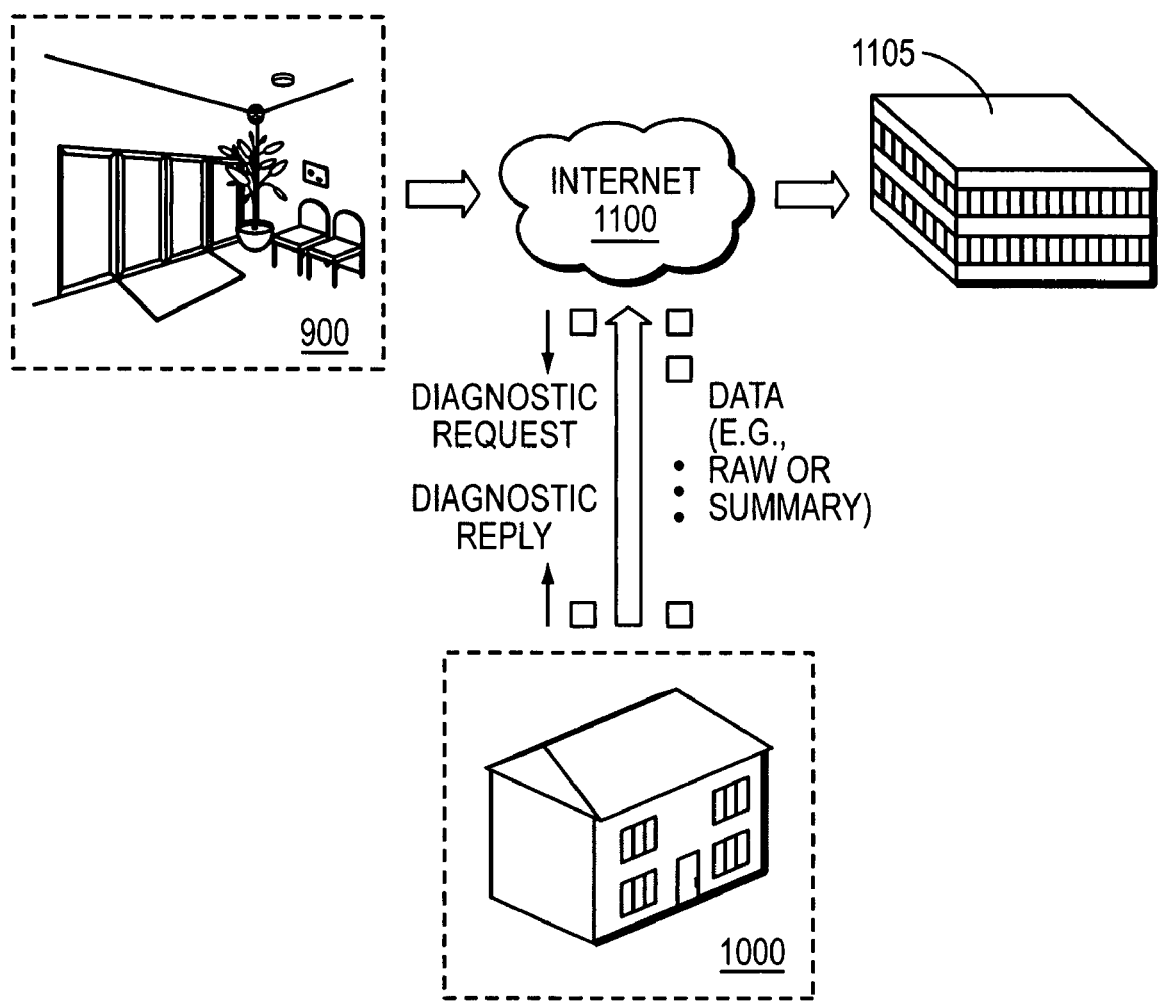
FIG. 11 is diagram illustrating a network of multiple sensor systems (not shown) connected to the Internet or other network, such as a wireless network (not shown), to monitor the status of sensors in an office lobby and a home from a remote location where the Internet or other network can be accessed.

FIG. 11 is diagram illustrating a network of multiple sensor systems (not shown) connected to the Internet 1100 or other network, such as a wireless network (not shown), to monitor the status of sensors 105 in an office lobby 900 and a home 1000 from a remote location 1105 where the Internet 1100 or other network can be accessed. In this example network environment, data communications, such as communications packets, can be employed to provide raw data (e.g., periods between pulses) or summary data (e.g., fault condition detected) from the sensor systems to a server (not shown) at the remote location 1105 configured to support the sensor systems.

Service models may be subscription-based and may include monitoring, diagnostics via two-way communications, repair, testing, etc. The communications may include any sort of diagnostic request known in the art, with an appropriate response sent in reply. Further, powerline communications may be employed to remotely turn off a heating pad left on for too long a period or left unattended at the initiation of a user or automatically initiated by a remote server as determiner by reported statistics sent by the heating pad. Moreover, email messages may be sent informing the owner of faults in the heating pad or the necessity of repair or replacement.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for measuring physical parameters, comprising:
    a plurality of sensors coupled in series having circuits with respective time constants relating to physical parameters to be measured by the sensors to cause respective measurement signals to be generated in series in a form of an effect on a drive signal as a function of the respective time constants; and
    a module to provide the drive signal to the sensors to generate the respective measurement signals and to measure the physical parameters based on a metric associated with the respective measurement signals.

2. The apparatus according to claim 1 wherein at least one sensor includes a circuit with a transducer that has a characteristic used to define the time constant.

3. The apparatus according to claim 2 wherein a combination of the transducer and an at least one passive circuit element defines the time constant.

4. The apparatus according to claim 3 wherein the at least one sensor further includes a component to change the time constant to affect the at least one metric associated with the respective measurement signal generated by the at least one sensor.

5. The apparatus according to claim 3 wherein the at least one sensor further includes a component to enable selectively changing the time constant from a first time constant to measure a first physical parameter by a given sensor to a second time constant to measure a second physical parameter by the same given sensor.

6. The apparatus according to claim 2 wherein the transducer is selected from a group consisting of: a temperature transducer, moisture transducer, pressure transducer, or switch.

7. The apparatus according to claim 1 wherein the physical parameter is selected from a group consisting of: temperature, moisture, pressure, or state change of a switch.

8. The apparatus according to claim 1 wherein the at least one metric includes at least one of the following: a pulse, period between pulses, amplitude, voltage, voltage change, or current.

9. The apparatus according to claim 1 further comprising:
    two wires electrically coupling the sensors and module via which the drive signal and measurement signals are transmitted between the sensors and module.

10. The apparatus according to claim 1 further comprising:
    at least three wires electrically coupling the sensors and module via which the drive signal and measurement signals are transmitted between the sensors and module.

11. The apparatus according to claim 1 wherein the module includes memory to store data used by the module to convert the metric to an operational parameter relating to the respective physical parameter, the module further including an interface to provide the operational parameter to a system configured to influence the physical parameters to be measured.

12. The apparatus according to claim 11 wherein the physical parameter is temperature of a heating pad.

13. The apparatus according to claim 1 wherein the module includes circuitry coupled to the sensors to generate pulses based on the measurement signals and wherein the module is configured to measure the physical parameters as a function of a time period between adjacent pulses.

14. The apparatus according to claim 1 wherein the module includes an interface to interact with a system that influences the physical parameters to be measured.

15. The apparatus according to claim 1 wherein the module is configured to provide the drive signal to the sensors by providing the drive signal to a first sensor in the series of sensors, which, in turn, is configured to provide a drive signal to a next sensor in the series of sensors, and so forth, except for the last sensor in the series.

16. The apparatus according to claim 15 wherein the sensors are configured to generate the effects on the drive signal in a manner that is measurable by the module.

17. A method for measuring physical parameters, comprising:
    generating a series of measurement signals representing respective physical parameters by affecting a drive signal at intervals meaningful of the physical parameters, the series of measurement signals generated as a function of the intervals; and
    measuring the physical parameters based on at least one metric associated with the respective measurement signals.

18. The method according to claim 17 wherein affecting the drive signal at intervals includes causing rapid increase in current of the drive signal at least in part due to charging an energy storage element at a beginning of each interval relative to a time toward an end of each interval.

19. The method according to claim 18 wherein affecting the drive signal includes increasing current draw of the drive signal at the intervals.

20. The method according to claim 19 further including:
changing the intervals at which the drive signal is affected meaningful of the physical parameters to affect the at least one metric associated with the respective measurement signal.

21. The method according to claim 19 further including:
changing the intervals at which the drive signal is affected to measure multiple physical parameters.

22. The method according to claim 17 wherein affecting the drive signal at intervals occurs at intervals as a function of at least one of the following: temperature, moisture, pressure, or a state change of a switch.

23. The method according to claim 17 wherein the physical parameter is selected from a group consisting of: temperature, state change of a switch, moisture, or pressure.

24. The method according to claim 17 wherein the at least one metric includes at least one of the following: a pulse, period between pulses, amplitude, voltage, voltage change, or current.

25. The method according to claim 17 further including:
conducting the drive signal and the series of measurement signals via two wires between a plurality of sensors generating the series of measurement signals by affecting the drive signal and a module providing the drive signal and measuring the series of measurement signals.

26. The method according to claim 17 further including:
conducting the drive signal and the series of measurement signals via at least three wires between a plurality of sensors generating the series of measurement signals by affecting the drive signal and a module providing the drive signal and measuring the series of measurement signals.

27. The method according to claim 17 further including:
storing data to convert the metric to operational parameters relating to the respective physical parameters;
converting the metric to the operational parameters; and
influencing the respective physical parameters as a function of the operational parameters.

28. The method according to claim 27 wherein the physical parameters are localized temperatures of a heating pad.

29. The method according to claim 17 further including:
generating pulses based on the measurement signals and measuring the physical parameters as a function of a time period between adjacent pulses.

30. The method according to claim 17 further including:
interacting with a system that influences the physical parameters to be measured.

31. The method according to claim 17 further including:
conducting the drive signal in series through a plurality of sensors generating the series of measurement signals until all measurement signals have been generated.

32. An apparatus for measuring temperature in a heating pad, comprising:
means for generating a series of measurement signals representing respective physical parameters by affecting a drive signal at intervals meaningful of the physical parameters, the series of measurement signals generated as a function of the intervals; and
means for measuring the physical parameters based on at least one metric associated with the respective measurement.

33. A heating pad system, comprising:
a heater element;
a driver unit to drive the heater element with a heater drive signal;
a plurality of thermal sensors coupled in series having circuits with respective time constants relating to the temperature of the heating pad measured by the thermal sensors to cause respective measurement signals to be generated in series in a form of an effect on a measurement drive signal as a function of the respective time constants, a metric associated with the measurement signals representative of the temperature measured by the respective thermal sensors; and
a module to monitor the measurement signals to sense the temperature measured by the thermal sensors and provide feedback to the driver unit to regulate a temperature produced by the heater element.

34. An apparatus for measuring the temperature in a heating pad, comprising:
a plurality of sensors coupled in series to sense respective physical parameters at the sensors; and
a module coupled to the sensors to provide a drive signal to the sensors and monitor effects on the drive signal caused at times defined by the sensors as a function of the respective physical parameters.

35. An apparatus for measuring physical parameters, comprising:
a first sensor having a first circuit with a respective first time constant relating to a physical parameter to be measured by the first sensor, the first circuit to cause generation of a first measurement signal in a form of an effect on a drive signal as a function of the first time constant;
a module coupled to the first sensor, the module to provide the drive signal to the first sensor to generate the first measurement signal in the form of the effect on the drive signal and to measure the physical parameter based on a metric associated with the first measurement signal; and
a second sensor coupled to the first sensor by a switch in the first sensor, the switch to enable transmission of the drive signal to the second sensor at a time determined by the physical parameter measured by the first sensor, the second sensor having a second circuit with a second time constant relating to a physical parameter to be measured by the second sensor, the second circuit to cause generation of a second measurement signal in a form of an effect on the drive signal as a function of the second time constant, the module to measure a second physical parameter based on a metric associated with the second measurement signal.

36. The apparatus of claim 35, wherein the physical parameter to be measured is temperature.

37. The apparatus of claim 35, wherein the physical parameter to be measured is temperature of a heating pad at the respective sensors.

* * * * *